(12) United States Patent
Morlet

(10) Patent No.: US 9,566,189 B2
(45) Date of Patent: Feb. 14, 2017

(54) GROOVED NEEDLE TIP FOR SURGICAL INSTRUMENT

(76) Inventor: Nigel Morlet, Mosman Park (AU)

( * ) Notice: Subject to any disclaimer, the term of this patent is extended or adjusted under 35 U.S.C. 154(b) by 382 days.

(21) Appl. No.: 14/236,748

(22) PCT Filed: Aug. 2, 2012

(86) PCT No.: PCT/AU2012/000915
§ 371 (c)(1),
(2), (4) Date: Feb. 3, 2014

(87) PCT Pub. No.: WO2013/016772
PCT Pub. Date: Feb. 7, 2013

(65) Prior Publication Data
US 2014/0243842 A1    Aug. 28, 2014

(51) Int. Cl.
*A61B 17/32* (2006.01)
*A61F 9/007* (2006.01)

(52) U.S. Cl.
CPC ................... *A61F 9/00745* (2013.01)

(58) Field of Classification Search
CPC .................................................. A61F 9/00745
See application file for complete search history.

(56) References Cited

U.S. PATENT DOCUMENTS

| | | |
|---|---|---|
| 2,711,733 A | 8/1951 | Jacoby, Jr. |
| 2,828,744 A | 4/1958 | Hirsch et al. |
| 3,071,135 A | 1/1963 | Baldwin et al. |
| 3,173,200 A | 3/1965 | Dunmire et al. |
| 3,589,363 A | 6/1971 | Banko |
| 4,490,139 A | 12/1984 | Huizenga et al. |
| 4,561,445 A | 12/1985 | Berke et al. |
| 4,689,040 A | 8/1987 | Thompson |
| 4,889,529 A | 12/1989 | Haindl |
| 4,959,049 A | 9/1990 | Smirmaul |
| 5,162,044 A | 11/1992 | Gahn et al. |
| 5,354,537 A | 10/1994 | Moreno |
| 5,515,871 A | 5/1996 | Bittner et al. |
| 5,653,724 A | 8/1997 | Imonti |
| 5,725,495 A | 3/1998 | Strukel et al. |
| 5,733,266 A | 3/1998 | Gravlee, Jr. |
| 5,788,679 A | 8/1998 | Gravlee, Jr. |
| 5,938,635 A | 8/1999 | Kuhle |

(Continued)

FOREIGN PATENT DOCUMENTS

| | | |
|---|---|---|
| DE | 196 28 252 | 1/1998 |
| DE | 199 42 693 | 3/2001 |

(Continued)

OTHER PUBLICATIONS

International—Type Search Report issued in National Application No. 2008904517, mailed Oct. 27, 2008—2 pages.

(Continued)

*Primary Examiner* — Gregory Anderson
(74) *Attorney, Agent, or Firm* — Hamre, Schumann, Mueller & Larson, P.C.

(57) ABSTRACT

A needle for a surgical instrument for removal of diseased or unwanted tissue is described. The needle has a hollow elongate needle shaft with a needle tip at a distal end for cutting tissue. The needle tip is flared in at least one plane and has a plurality of grooves milled into a surface of the tip in an asymmetric arrangement around the circumference of the needle tip.

23 Claims, 9 Drawing Sheets

DETAIL OF NEEDLE TIP

DETAIL E

(56) References Cited

U.S. PATENT DOCUMENTS

| | | |
|---|---|---|
| 5,968,022 A | 10/1999 | Saito |
| 5,993,408 A | 11/1999 | Zaleski |
| 5,997,499 A | 12/1999 | Sussman et al. |
| 6,007,555 A | 12/1999 | Devine |
| 6,159,175 A | 12/2000 | Strukel et al. |
| 6,165,150 A | 12/2000 | Banko |
| 6,283,974 B1 | 9/2001 | Alexander |
| 6,299,591 B1 | 10/2001 | Banko |
| 6,398,759 B1 | 6/2002 | Sussman et al. |
| 6,533,750 B2 | 3/2003 | Sutton et al. |
| 7,588,553 B2 | 9/2009 | Dewey |
| 8,187,203 B2 * | 5/2012 | McClellan ......... A61B 10/0266 600/562 |
| 8,568,422 B2 | 10/2013 | Morlet |
| 2002/0156492 A1 | 10/2002 | Timm et al. |
| 2004/0193121 A1 | 9/2004 | Kadziauskas et al. |
| 2004/0215206 A1 | 10/2004 | Kadziauskas et al. |
| 2005/0020990 A1 | 1/2005 | Akahoshi |
| 2006/0052758 A1 | 3/2006 | Dewey |
| 2006/0217672 A1 | 9/2006 | Chon |
| 2006/0253056 A1 | 11/2006 | Kadziauskas et al. |
| 2007/0260199 A1 | 11/2007 | Rockley |
| 2008/0058708 A1 | 3/2008 | Akahoshi |
| 2008/0139994 A1 | 6/2008 | Mackool et al. |
| 2008/0188792 A1 | 8/2008 | Barrett |
| 2009/0099536 A1 | 4/2009 | Akahoshi |
| 2009/0137971 A1 | 5/2009 | Akahoshi |
| 2009/0192440 A1 | 7/2009 | Akahoshi |
| 2011/0046541 A1 | 2/2011 | Akahoshi |
| 2013/0023918 A1 | 1/2013 | Morlet |

FOREIGN PATENT DOCUMENTS

| | | |
|---|---|---|
| EP | 0 619 993 | 10/1994 |
| EP | 0 962 205 | 12/1999 |
| EP | 1 464 310 | 10/2004 |
| EP | 1 532 996 | 5/2005 |
| JP | 2006-000644 | 1/2006 |
| JP | 2008-154842 | 7/2008 |
| JP | 2008-154843 | 7/2008 |
| WO | 94/22402 | 10/1994 |
| WO | 00/74615 | 12/2000 |
| WO | 2005/025434 | 3/2005 |
| WO | 2005/032439 | 4/2005 |
| WO | 2007/119107 | 10/2007 |
| WO | 2008/147771 | 12/2008 |
| WO | 2009/000959 | 12/2008 |
| WO | 2010/022460 | 3/2010 |
| WO | 2011/120080 | 10/2011 |

OTHER PUBLICATIONS

International—Type Search Report issued in National Application No. 2010901302, mailed Jul. 1, 2010—2 pages.
International—Type Search Report issued in National Application No. 2010901302, mailed Aug. 12, 2010—2 pages.
International Search Report issued in International Application No. PCT/AU2009/001109, mailed Oct. 28, 2009—5 pages.
International—Type Search Report issued in National Application No. 2011903103, mailed Jun. 7, 2012—3 pages.
International Search Report issued in International Application No. PCT/AU2011/000352, mailed Jun. 17, 2011—6 pages.
International Search Report issued in International Application No. PCT/AU2012/000915, mailed Aug. 31, 2012—5 pages.

* cited by examiner

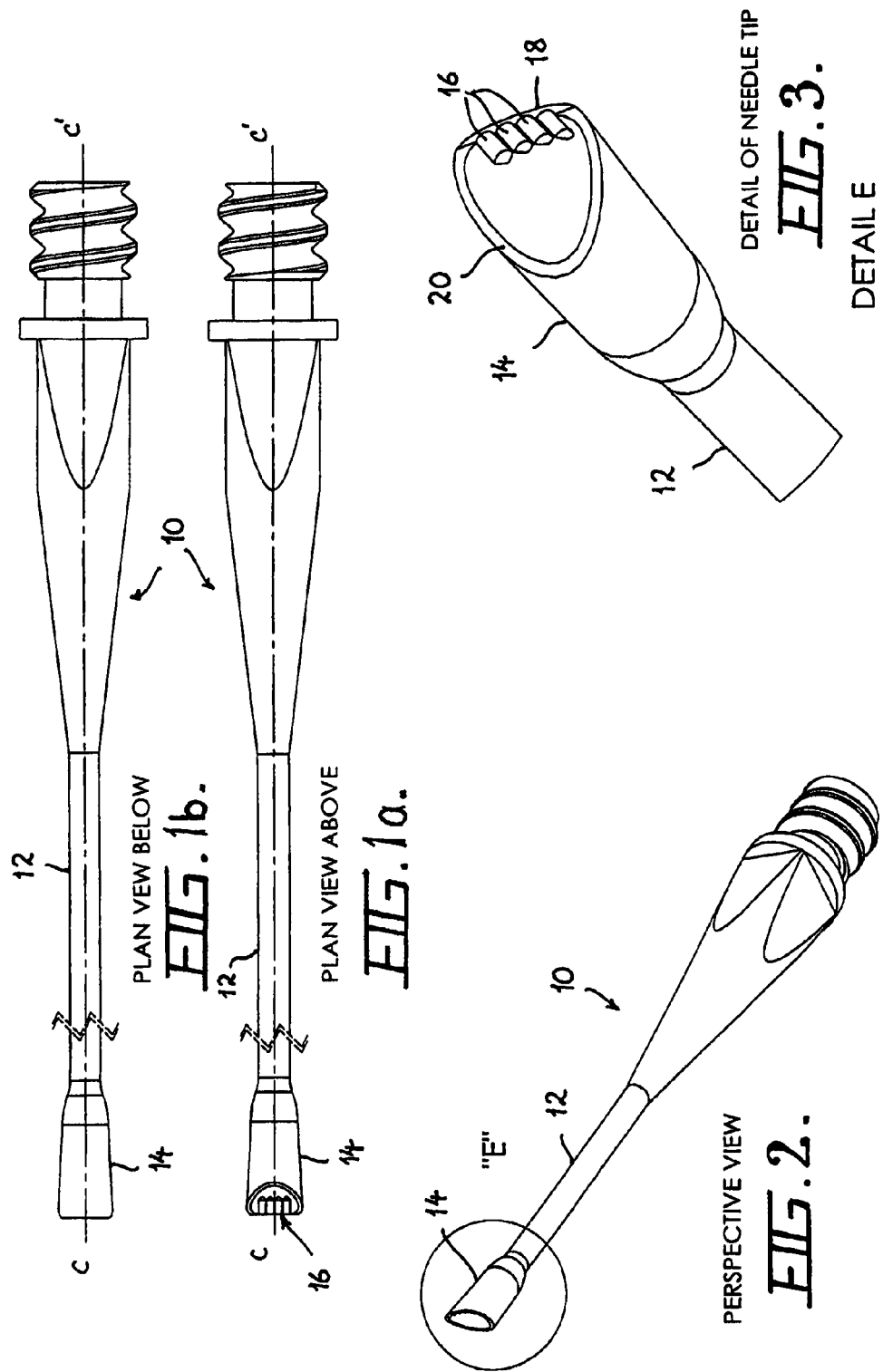

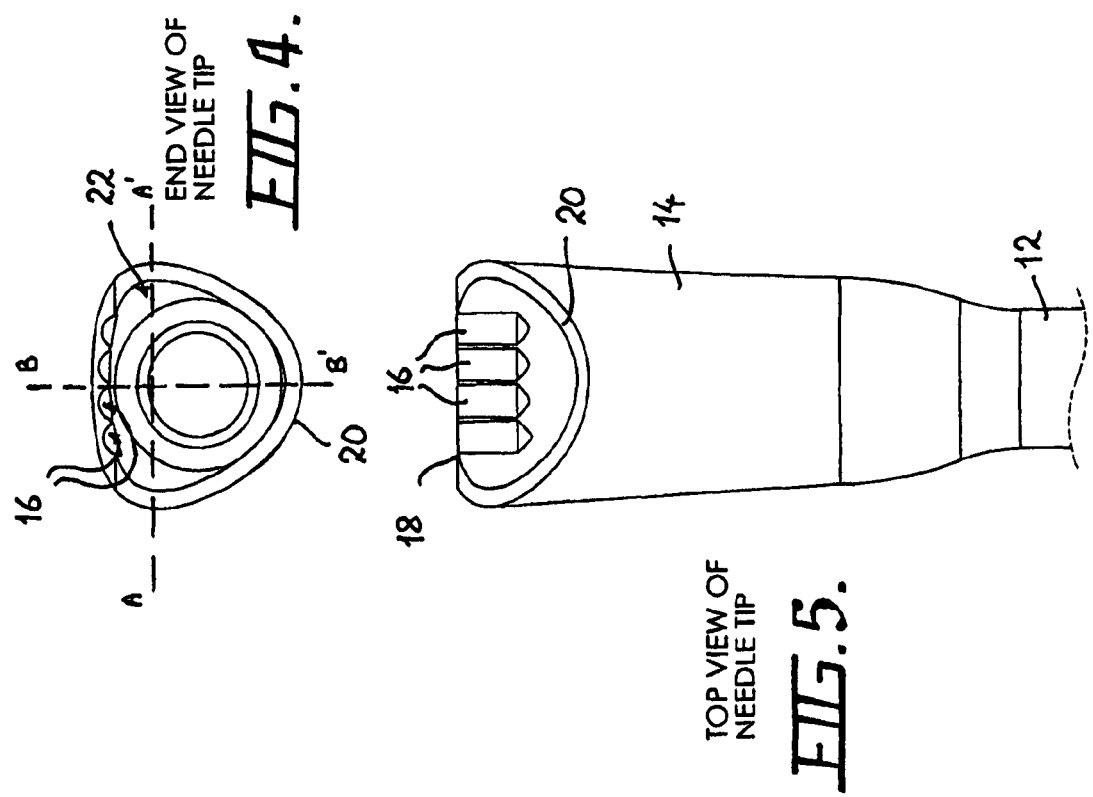

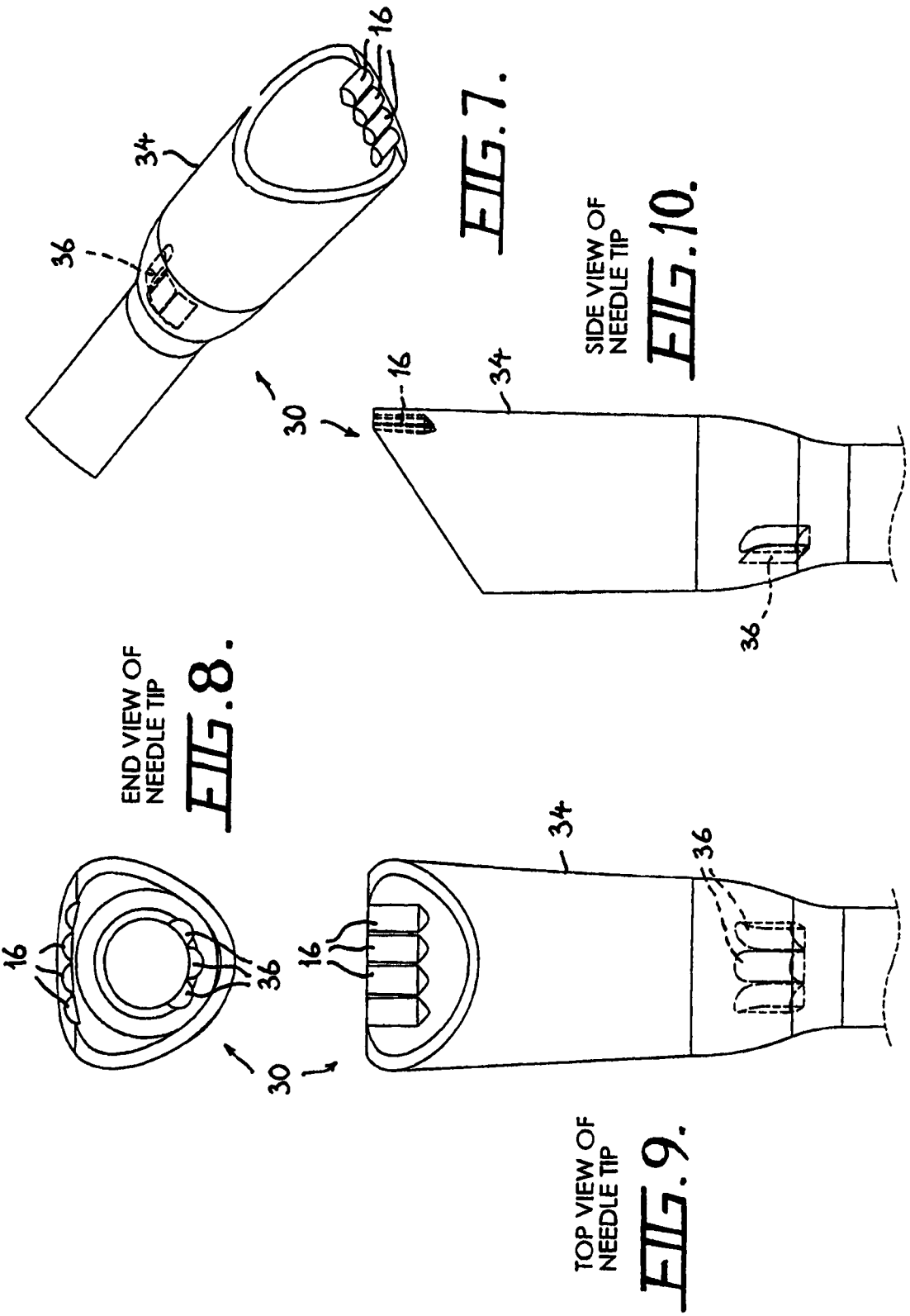

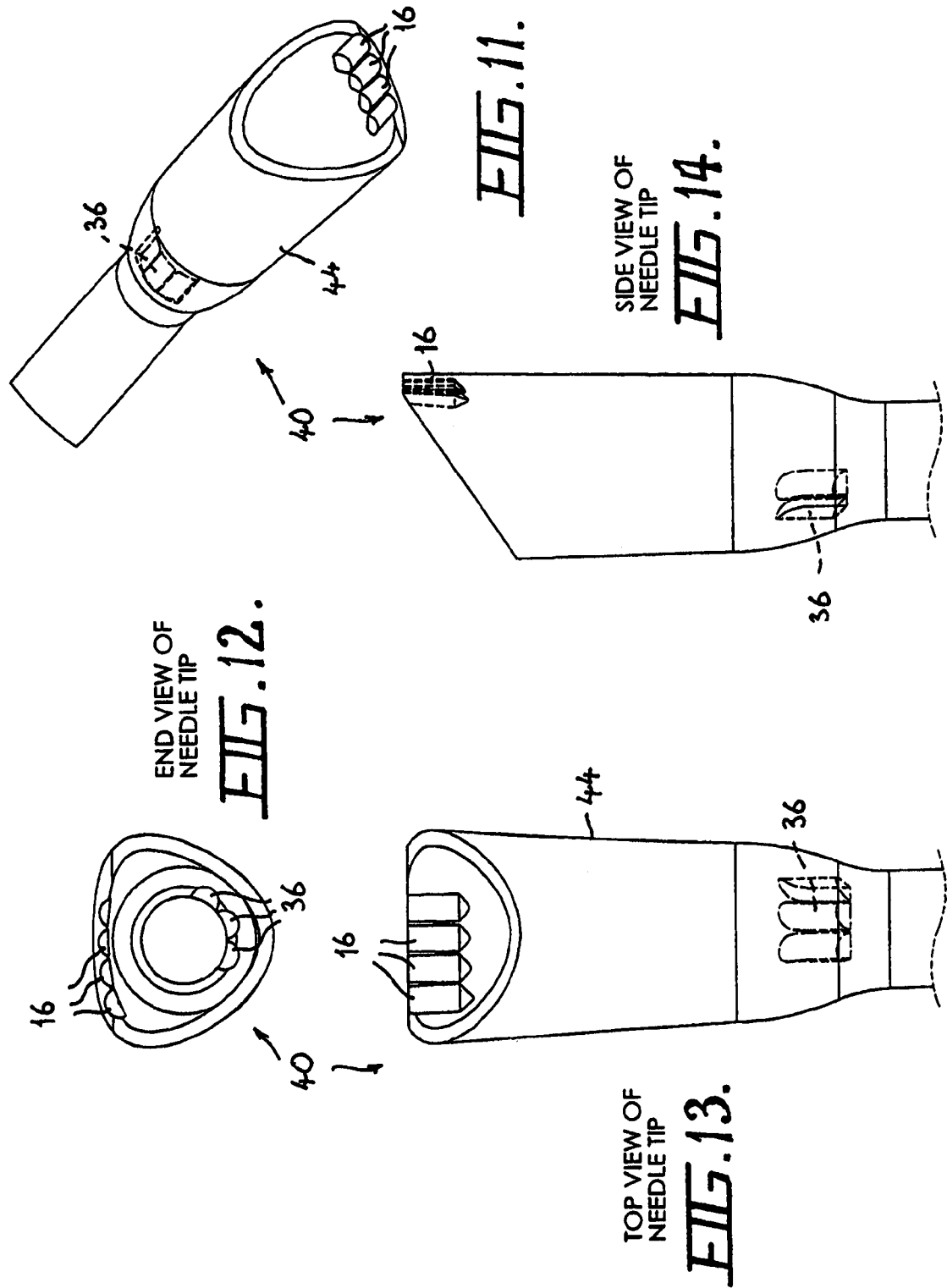

SIDE VIEW OF NEEDLE TIP

END VIEW OF NEEDLE TIP

TOP VIEW OF NEEDLE TIP

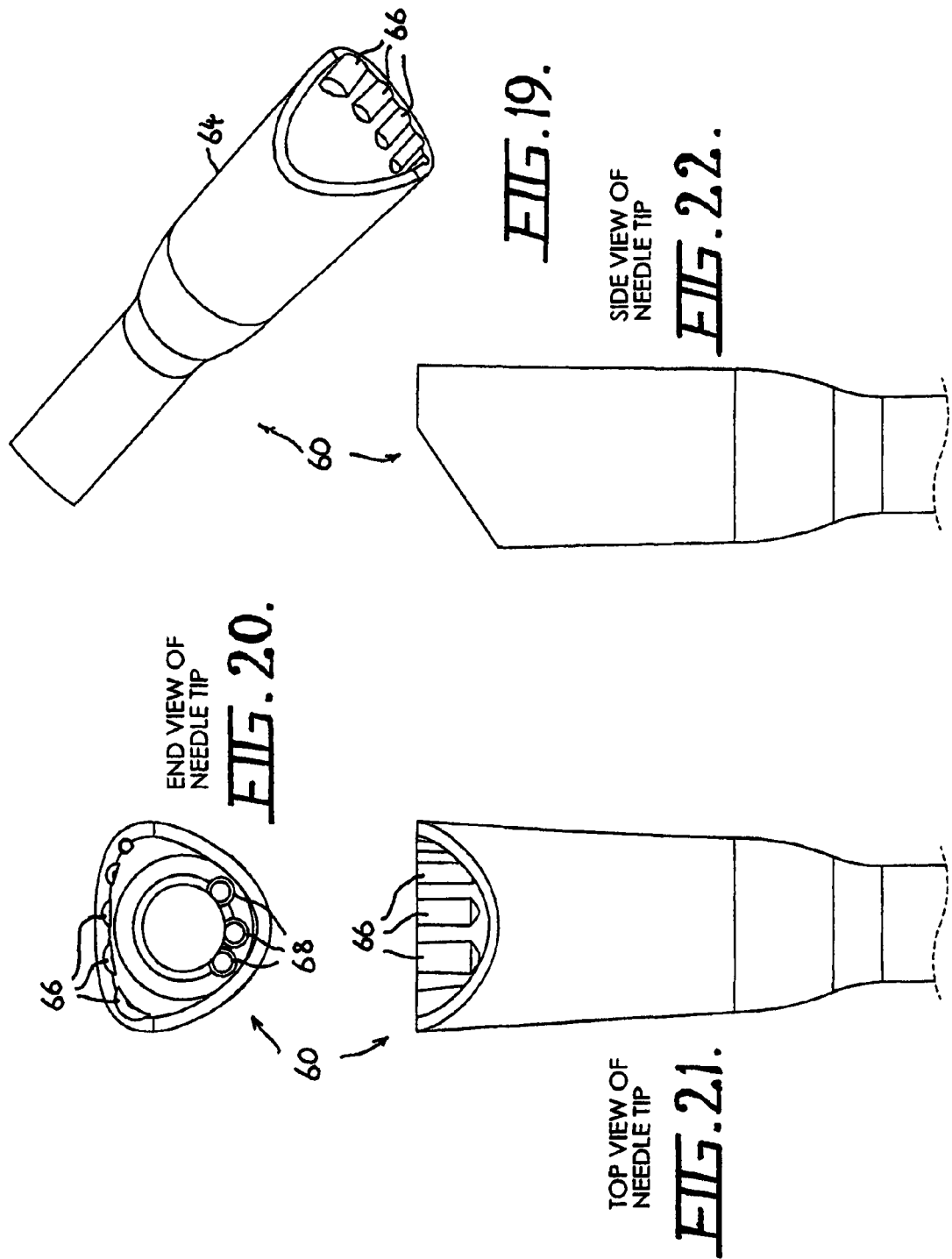

GROOVED NEEDLE TIP FOR SURGICAL INSTRUMENT

FIELD OF THE INVENTION

The present invention relates to a needle tip for a surgical instrument and relates particularly, though not exclusively, to a grooved needle tip for an ultrasonic surgical instrument of the kind used for phacoemulsification in surgical cataract removal procedures.

BACKGROUND TO THE INVENTION

Ophthalmologists have developed surgical cataract removal procedures which involve removal of the crystalline lens and replacement with an artificial lens through a small incision in the capsular bag in which the lens material is contained. Charles Kelman and Anton Banko were among the first to successfully develop a technique for removal of cataracts using a handheld surgical instrument with a hollow needle vibrating at ultrasonic frequencies. U.S. Pat. No. 3,589,363 describes their ground-breaking technique. This technique, which has become known as phacoemulsification, involves inserting a needle tip vibrating at ultrasonic frequencies into the eye through a small corneal incision. As the vibrating needle tip and ultrasonic wave contacts the lens material it disintegrates and emulsifies it with an irrigating fluid. A coaxial sleeve over the needle or a second canula delivers the irrigating fluid, and the disintegrated lens disperses to form an emulsion which is aspirated through the hollow interior of the needle.

Depending on the extent of the cataract formation the diseased lens material can vary considerably in hardness and/or density. The harder or more dense the diseased material the more difficult it is to remove using phacoemulsification. Various types of ultrasonic vibration have been tried to improve the rate and efficiency of emulsification; previously using longitudinal alone, but recently using transverse and torsional vibration, as well as combinations thereof. In addition, many have developed alternative needle and tip configurations to try to improve on the standard round needle with a bevelled tip. For example, tips that are flared to produce an "acoustic horn" to focus the ultrasonic sound waves. Yet other examples use transverse steps or "baffles", or concave recesses within the mouth of the tip to enhance cavitation and emulsification.

The effect of these tip modifications with transverse or torsional ultrasound is limited because the designs were principally for longitudinal movement of the needle. A standard round tip on a straight needle cannot work with torsional ultrasound handpieces; the rotary tip motion produced simply "cores" out the material rather than breaking and emulsifying it. The bent needle that Kelman developed is used because it transforms the rotary needle motion into a sweeping or "scything" tip motion. However this type of bent needle has poor ergonomics and can be difficult to use during phacoemulsification surgery. Because of poor tip cutting efficiency, it is also easily blocked with incompletely emulsified lens material.

The present invention was developed to providing a needle tip configuration with better phacoemulsification efficiency, principally for torsional and transverse ultrasonic handpieces without compromising linear phacoemulsification. It will be appreciated, that the same type of needle tip may also be used for other types of surgical procedure such as removal of tumours (e.g. brain tumours), liposuction, or in dentistry. Therefore the invention is not limited in its application to phacoemulsification.

References to prior art in this specification are provided for illustrative purposes only and are not to be taken as an admission that such prior art is part of the common general knowledge in Australia or elsewhere.

SUMMARY OF THE INVENTION

According to one aspect of the present invention there is provided a needle for a surgical instrument for removal of diseased or unwanted tissue, the needle comprising:

a hollow elongate needle shaft having a needle tip at a distal end for cutting tissue, the needle tip being flared in at least one plane and having a plurality of grooves milled into a surface of the tip in an asymmetric arrangement around the circumference of the needle tip.

Preferably the grooves are milled into an internal surface of the tip. Preferably the grooves are milled into a part of the internal surface adjacent and/or extending to an edge of a lip of the tip mouth. Preferably the grooves extend substantially perpendicularly to the edge of the lip. As another option the grooves may extend substantially transversely to the edge of the lip.

Preferably the grooves are milled into a part of the throat of the tip, where the tip is joined to the needle shaft. Typically the grooves are milled into a part of the back of the throat.

Typically the grooves are straight and substantially parallel to each other. Preferably the grooves are of all substantially equal width and length. Alternatively the grooves may be of unequal width. Preferably the grooves are spaced from each other at substantially equal intervals. Alternatively the grooves may be spaced from each other at unequal intervals. The grooves may be of a size and shape to create a scalloped effect.

In one preferred form of the invention the tip has a plurality of grooves milled into both the lip and the throat of the tip.

Preferably the tip has a flattened posterior lip and an anterior lip shaped to produce an asymmetric tip mouth with a major axis larger than an outer diameter of the needle shaft and a minor axis smaller than the major axis. Advantageously the grooves are milled into a surface of the posterior lip.

Preferably the anterior lip is curved to produce a substantially D-shaped tip mouth.

Typically the flattened posterior lip is on an edge of a posterior surface that lies in a plane that is substantially parallel to a central longitudinal axis of the needle shaft. Preferably the needle tip has a central longitudinal axis (the tip axis) which is substantially parallel to the central longitudinal axis of the needle shaft. In one embodiment the anterior lip of the tip mouth is also flattened and is on the edge of an anterior surface that lies in a plane that is substantially parallel to a central longitudinal axis of the needle shaft.

Preferably the substantially D-shaped tip mouth lies in a plane that is substantially orthogonal to a central longitudinal axis (the needle axis) of the needle shaft. Advantageously the posterior lip is substantially transverse to the minor axis of the tip mouth and is on the edge of the posterior surface which is substantially parallel to the major axis of the tip mouth.

According to another aspect of the present invention there is provided a needle for a surgical instrument for removal of diseased or unwanted tissue, the needle comprising:

a hollow elongate needle shaft having a needle tip at a distal end for cutting tissue, the needle tip having a substantially transverse groove milled into a lip of the tip.

Preferably the transverse groove is milled in an asymmetric arrangement around the circumference of the needle tip. Preferably the transverse groove is milled into an edge of the lip to form a stepped edge at the mouth of the tip. Preferably the transverse groove is one of a plurality of transverse grooves milled into the edge of the lip.

According to a still further aspect of the present invention there is provided a needle for a surgical instrument for removal of diseased or unwanted tissue, the needle comprising:

a hollow elongate needle shaft having a needle tip at a distal end for cutting tissue, the needle tip being flared in at least one plane and wherein an outside flare angle is less than an internal flare angle to create a wall of variable thickness in a mouth of the tip.

Throughout the specification, unless the context requires otherwise, the word "comprise" or variations such as "comprises" or "comprising", will be understood to imply the inclusion of a stated integer or group of integers but not the exclusion of any other integer or group of integers. Likewise the word "preferably" or variations such as "preferred", will be understood to imply that a stated integer or group of integers is desirable but not essential to the working of the invention.

BRIEF DESCRIPTION OF THE DRAWINGS

The nature of the invention will be better understood from the following detailed description of several specific embodiments of a needle tip for a surgical instrument, given by way of example only, with reference to the accompanying drawings, in which:

FIGS. 1 (a) and 1 (b) are a top plan view and a bottom plan view respectively of a first embodiment of a surgical needle in accordance with the present invention;

FIG. 2 is a bottom perspective view of the needle of FIG. 1;

FIG. 3 is a detail view of the needle tip of the needle of FIG. 2;

FIG. 4 is an end view looking into the mouth the needle tip of the needle of FIG. 1;

FIG. 5 is a top plan view of the needle tip of FIG. 3;

FIG. 6 is a side view of the needle tip of FIG. 3;

FIG. 7 is a perspective view of a second embodiment of a needle tip in accordance with the present invention;

FIG. 8 is an end view looking into the mouth of the needle tip of FIG. 7;

FIG. 9 is a top plan view of the needle tip of FIG. 7;

FIG. 10 is a side view of the needle tip of FIG. 7;

FIG. 11 is a perspective view of a third embodiment of a needle tip in accordance with the present invention;

FIG. 12 is an end view looking into the mouth of the needle tip of FIG. 11;

FIG. 13 is a top plan view of the needle tip of FIG. 11;

FIG. 14 is a side view of the needle tip of FIG. 11;

FIG. 19 is a perspective view of a fifth embodiment of a needle tip in accordance with the present invention;

FIG. 20 is an end view looking into the mouth of the needle tip of FIG. 19;

FIG. 21 is a top plan view of the needle tip of FIG. 19;

FIG. 22 is a side view of the needle tip of FIG. 19;

DETAILED DESCRIPTION OF PREFERRED EMBODIMENTS

Figure 15:
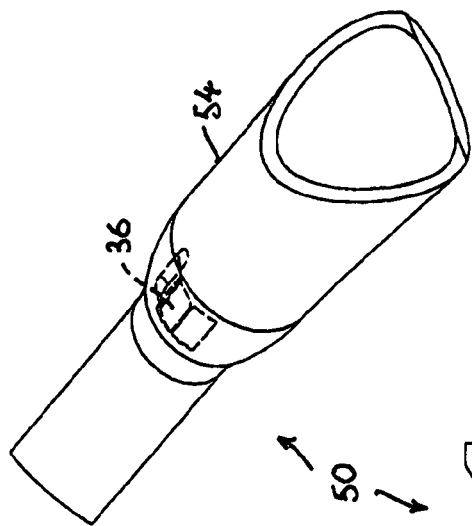
FIG. 15 is a perspective view of a fourth embodiment of a needle tip in accordance with the present invention.
Figure 17:
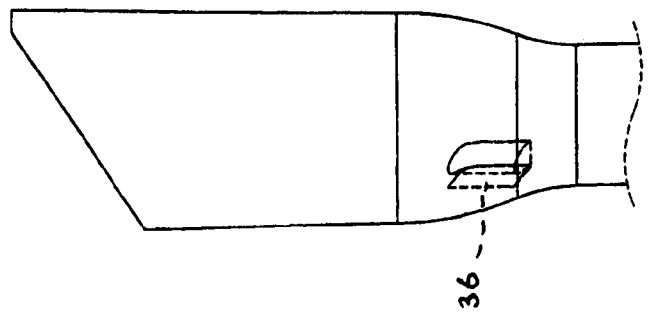
FIG. 17 is a side view of the needle tip of FIG. 15.
Figure 18:
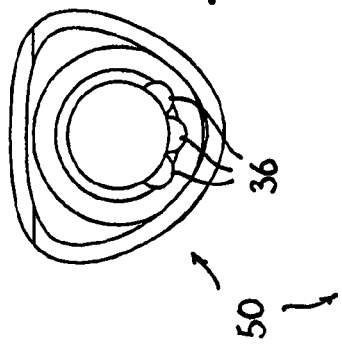
FIG. 18 is an end view looking into the mouth of the needle tip of FIG. 15.
Figure 16:
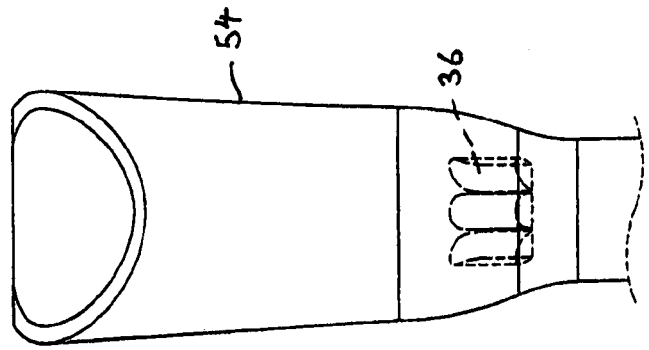
FIG. 16 is a top plan view of the needle tip of FIG. 15.

A first embodiment of a needle 10 for a surgical instrument for removal of diseased or unwanted tissue in accordance with the invention is illustrated in FIG. 1. The needle 10 comprises a hollow elongate needle shaft 12 having a needle tip 14 for cutting tissue at a distal end of the needle shaft 12. The needle tip 14 is flared in at least one plane and has a plurality of grooves 16 milled into an internal surface of the tip. The grooves 16 are provided in an asymmetric arrangement around the circumference of the needle tip.

In the illustrated embodiment the tip 14 has a flattened posterior lip 18 and a curved anterior lip 20 shaped to produce an asymmetric tip mouth 22 with a major axis A-A' larger than an outer diameter of the needle shaft 12 and a minor axis B-B' smaller than the major axis (as shown in FIG. 4). In this embodiment the anterior lip 20 is curved to produce a substantially D-shaped tip mouth 22, when viewed in a plane that is substantially orthogonal to a central longitudinal axis C-C' (the needle axis) of the needle 10. The D-shaped tip mouth is particularly advantageous as it is optimised for torsional motion. However it will be understood that the tip 14 may be of any desirable shape, and is not limited to having a D-shaped tip mouth as in the illustrated embodiments.

Throughout this specification the term "posterior" refers to the lip, or surface, or edge that is situated at the back of the needle tip, or most distant in the surgeon's line of sight, when viewed in normal operation. In other words the posterior lip (lip 18 in FIG. 3) is generally the leading or cutting edge of the needle tip, which first enters the tissue of the eye. The term "anterior" thus refers to the opposite lip or surface, namely that which is situated on the front of the needle tip, or nearest in the surgeon's line of sight, when viewed in normal operation. In other words the anterior lip (lip 20 in FIG. 3) is generally the trailing edge of the needle tip, which last enters the tissue of the eye.

Preferably the grooves 16 are milled into a part of the internal surface adjacent and extending to an edge of the flattened posterior lip 18 of the tip mouth 22. Preferably the grooves 16 extend substantially perpendicularly to the edge of the lip 18. The edges of the milled grooves 16 help to prevent clogging at the tip mouth 22. By providing grooves 16 on only part of the internal lip surface, the formation of ultrasonic standing waves and harmonics is inhibited. The grooves 16 also enhance the fluidics at the tip mouth 22 to create better flow of irrigating fluid and emulsified tissue into the tip. The edges of the grooves 16 also provide additional cutting edges in the tip mouth 22, particularly during torsional motion of the tip.

A second embodiment of a needle 30 for a surgical instrument for removal of diseased or unwanted tissue in accordance with the invention is illustrated in FIGS. 7 to 10. The needle 30 is similar to the first embodiment of FIGS. 1 to 6, and therefore the similar parts will be identified using the same reference numerals, and will not be described again in detail. The principal difference in the needle 30 is that a plurality of grooves 36 are also milled into a part of the throat of the needle tip 34, where the tip 34 is joined to the needle shaft 12. Typically the grooves 36 are milled into the back of the throat of the needle tip 34.

As with the grooves 16, the edges of the milled grooves 36 help to prevent clogging of the tip throat, which is an issue for current tips using torsional motion. By providing grooves 36 on only part of the internal throat surface the formation of ultrasonic standing waves and harmonics is inhibited. The grooves 36 also enhance the turbulence in the tip throat to create better flow of irrigating fluid and emulsified tissue.

Typically the grooves 16 and 36 are straight and substantially parallel to each other. In these two embodiments the grooves 16 and 36 are all substantially equal in width and length. Furthermore, in the first two embodiments, whilst the arrangement of the grooves 16 and 36 is asymmetrical about the major axis A-A' of the tip mouth, it is substantially symmetrical about the minor axis B-B' of the tip mouth.

A third embodiment of a needle 40 for a surgical instrument for removal of diseased or unwanted tissue in accordance with the invention is illustrated in FIGS. 11 to 14. The needle 40 is similar to the second embodiment of FIGS. 7 to 10, and therefore the similar parts will be identified using the same reference numerals, and will not be described again in detail. The principal difference in the needle 40 is that the arrangement of the grooves 16 and 36 is asymmetrical about both the major axis A-A' and the minor axis B-B' of the tip mouth. As can be seen most clearly in FIGS. 12 and 13, both the lip grooves 16 and the throat grooves 36 are offset from the minor axis B-B' of the tip mouth. The grooves 16 and 36 enhance the emulsification and fluidics of the tip mouth, prevent clogging, as well as inhibiting interruption to flow from standing waves and other harmonics within the tip mouth and throat.

A fourth embodiment of a needle 50 for a surgical instrument for removal of diseased or unwanted tissue in accordance with the invention is illustrated in FIGS. 15 to 18. The needle 50 is similar to the second embodiment of FIGS. 7 to 10, and therefore the similar parts will be identified using the same reference numerals, and will not be described again in detail. The principal difference in the needle 50 is that it is provided with throat grooves 36 only. There may be some types of needle tip where it is preferable not to have grooves on the internal lip surface, but where the provision of throat grooves 36 may still be advantageous for the reasons given above. Clearly the arrangement of the throat grooves 36 in the tip 54 may also be asymmetrical about the minor axis B-B'.

A fifth embodiment of a needle 60 for a surgical instrument for removal of diseased or unwanted tissue in accordance with the invention is illustrated in FIGS. 19 to 22. The needle 60 is similar to the second embodiment of FIGS. 7 to 10, and therefore the similar parts will be identified using the same reference numerals, and will not be described again in detail. In all of the previously described embodiments the grooves are spaced from each other at substantially equal intervals. The principal difference in the needle 60 is that a plurality of lip grooves 66 and throat grooves 68 are arranged with a differential random spacing from each other.

Furthermore, whereas in the previous embodiments the grooves are all of similar shape and configuration, in this fifth embodiment the lip grooves 66 are of varying depths and widths, as can be seen most clearly in FIGS. 20 and 21. Likewise, the throat grooves 68 of this embodiment are different from that of the previous embodiments. This illustrates the kinds of variations and modifications that can be made to the shape and configuration of the grooves, without departing from the main inventive concept. It will be understood that the grooves may also be milled into the internal surfaces so as to be of varying lengths and depths.

Figure 23:
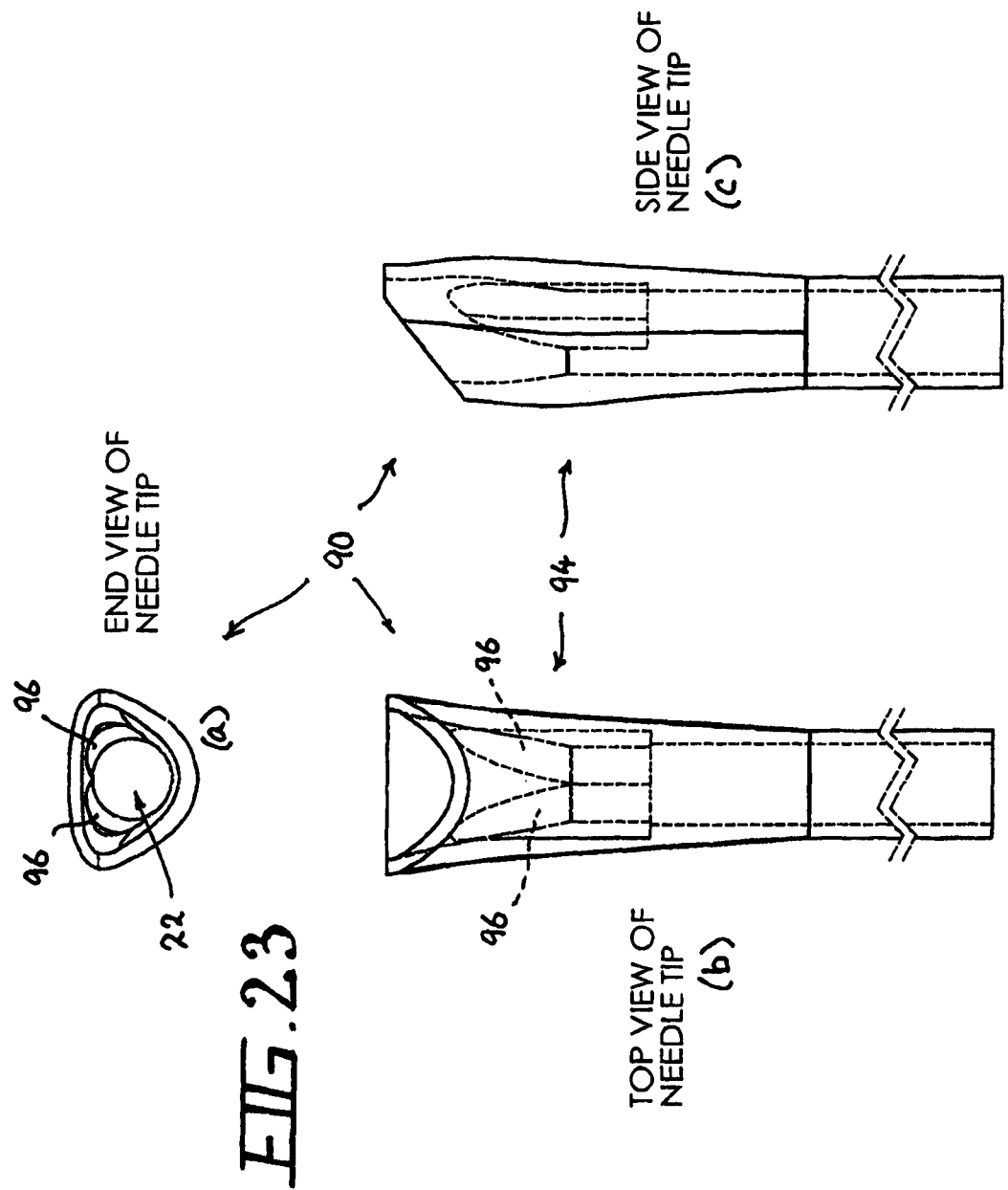
FIGS. 23 (a), (b) and (c) are an enlarged end view, top view and side view respectively of a sixth embodiment of a needle tip in accordance with the present invention.

A sixth embodiment of a needle 90 for a surgical instrument for removal of diseased or unwanted tissue in accordance with the invention is illustrated in FIG. 23. The needle 90 is similar to the first embodiment of FIGS. 1 to 6, and therefore the similar parts will be identified using the same reference numerals, and will not be described again in detail. One difference is in the nature of the flare, which in this embodiment is more gradual from the point where the throat of the needle tip 94 joins the needle shaft to the mouth 22 of the tip.

The main difference in this embodiment is in the number, length and shape of a pair of grooves 96 milled into an internal surface of the tip 94. Grooves 96 do not extend to the edge of the lip and are about midway between the throat of the tip and the tip mouth 22. As with the previous embodiments, the grooves 96 extend substantially perpendicularly to the edge of the lip 18, but are wider and longer to create a scalloped effect. The edges of the milled grooves 96 help to prevent clogging at the tip mouth 22. By providing grooves 96 on only part of the internal lip surface, the formation of ultrasonic standing waves and harmonics is inhibited. The grooves 96 enhance the fluidics at the tip mouth 22 to create better flow of irrigating fluid and emulsified tissue into the tip throat. The edges of the grooves 96 also provide additional cutting edges in the tip mouth 22, particularly during torsional motion of the tip.

Figure 25:
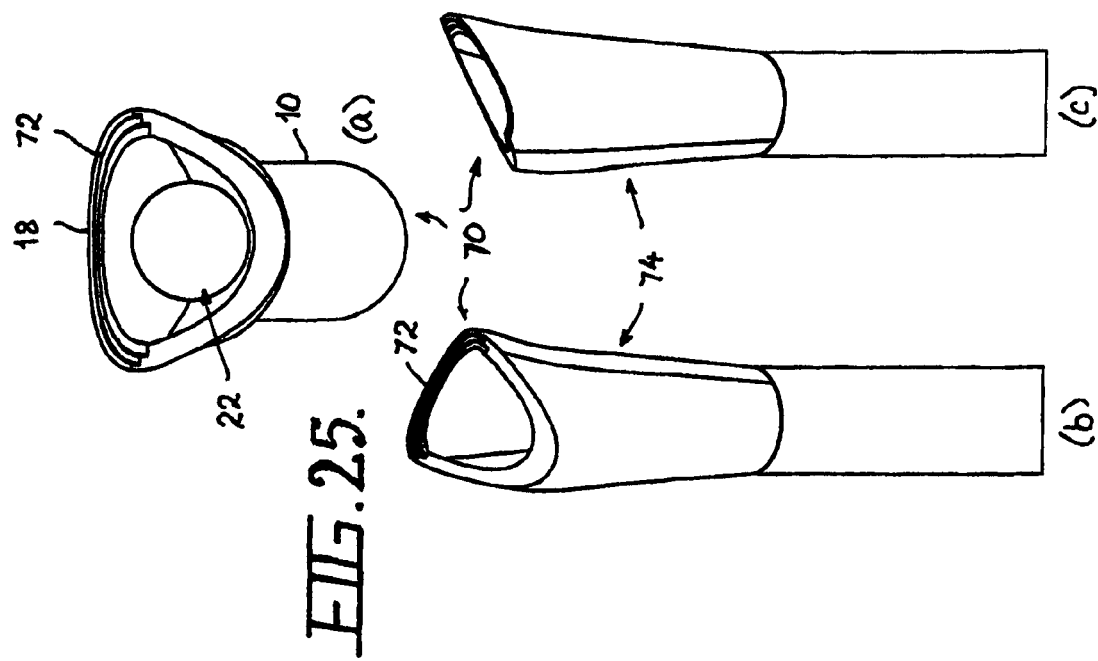
FIGS. 25 (a), (b) and (c) are an end perspective view, a top perspective view and a side perspective view respectively of the needle tip of FIG. 24.
Figure 24:
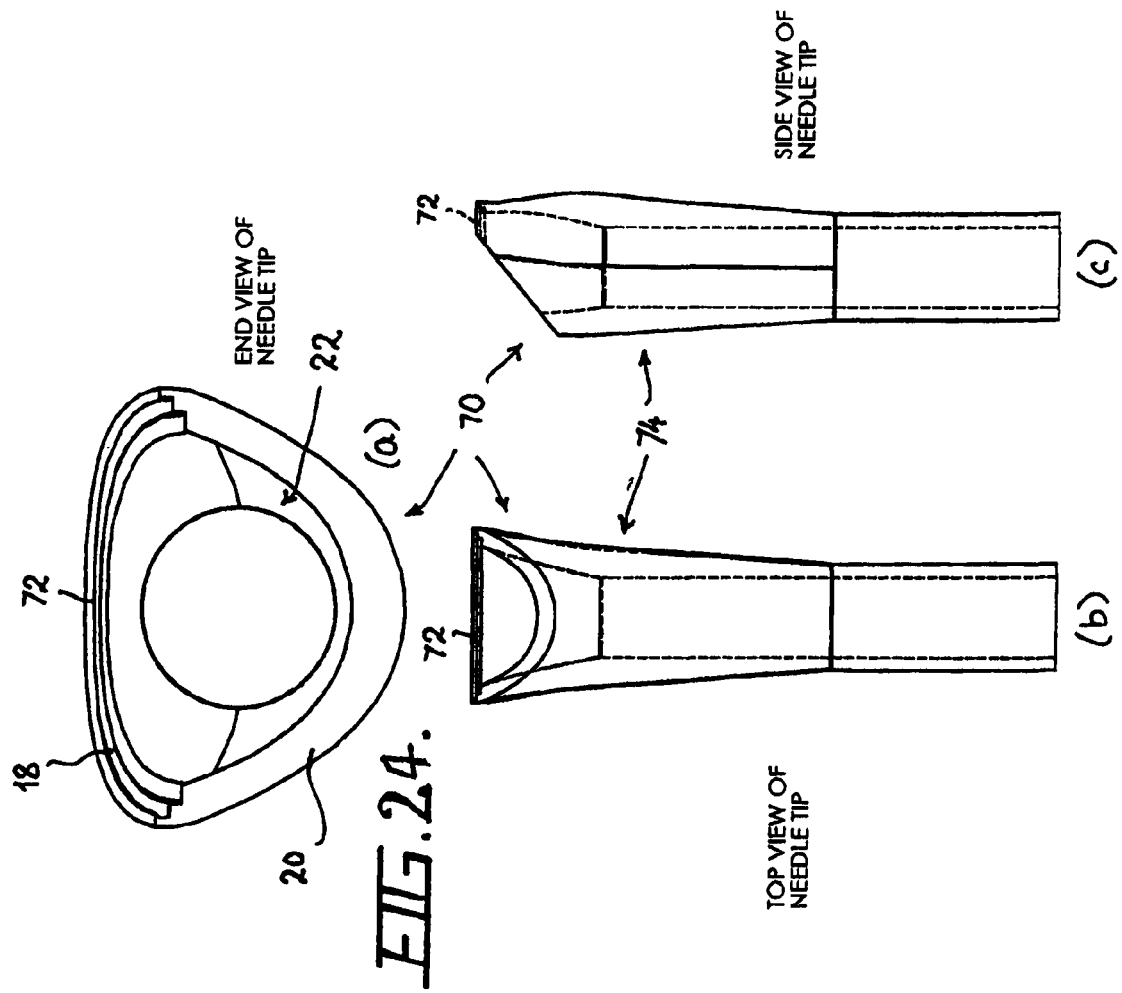
FIGS. 24 (a), (b) and (c) are an enlarged end view, top view and side view respectively of a seventh embodiment of a needle tip in accordance with the present invention.

A seventh embodiment of a needle 70 for a surgical instrument for removal of diseased or unwanted tissue in accordance with the invention is illustrated in FIGS. 24 and 25. The needle 70 is similar to the first embodiment of FIGS. 1 to 6, and therefore the similar parts will be identified using the same reference numerals, and will not be described again in detail. The most important difference in the needle 70 is that a plurality of substantially transverse grooves 72 is milled into a lip of the tip. In this embodiment the transverse grooves are provided in an asymmetric arrangement around the circumference of the needle tip 74. The transverse grooves 72 are cut substantially perpendicular to the tip axis. However the transverse grooves may also be cut at an acute angle to the tip axis to create a sharper stepped edge on the posterior lip 18, to further enhance the cutting action.

The transverse grooves 72 are milled into an edge of the posterior lip 18 to form a stepped edge at the mouth of the tip 74. In the illustrated embodiment a plurality of transverse grooves 72 is milled into the edge of the lip; however a single groove may also be advantageous. During the manufacturing process, each transverse groove 72 is typically milled with a micro-lathe that cuts the groove into the internal edge of the tip mouth, about the entire circumference of the tip mouth. When a chamfer 78 is cut on the tip mouth, at an acute angle to the tip axis as can be seen most clearly in FIGS. 24 (*c*) and 25 (*c*), this produces the asymmetric arrangement of the transverse grooves 72 about the circumference of the needle tip. The subsequent flattening of the posterior lip 18 and the curved anterior lip 20 produce a D-shaped tip mouth 22, as can be seen most clearly in FIGS. 24 (a) and 25 (a).

It will be understood that one or more transverse grooves 72 may also be cut into a lip of a needle tip having a different shape from that illustrated. Furthermore it is not necessarily essential that the transverse grooves be milled in an asymmetric arrangement about the circumference of the needle tip. In the illustrated embodiment the asymmetric arrangement is designed to optimise the cutting action during torsional vibration of the needle tip; however the transverse grooves will also enhance the cutting action during longitudinal vibration. Each transverse groove 72 provides an additional cutting edge at the stepped edge of the tip mouth, which increases the cutting efficiency of the needle tip 74.

In both of the sixth and seventh embodiments of FIGS. 23 to 25, another significant feature is that the external flare of the tip is less acute than the internal flare of the tip. This provides for increased wall thickness in the throat region of the tip, importantly in the rear of the throat. Increased thickness in the proximal throat near the neck allows for a variable (asymmetric) depth of each groove as it progresses proximally from the mouth opening. This configuration also creates a deep transverse step where the throat meets the neck of the needle. The deeper recess of the back of the throat increases the turbulence in the throat improving tissue emulsification and the needle fluidics.

Figure 27:
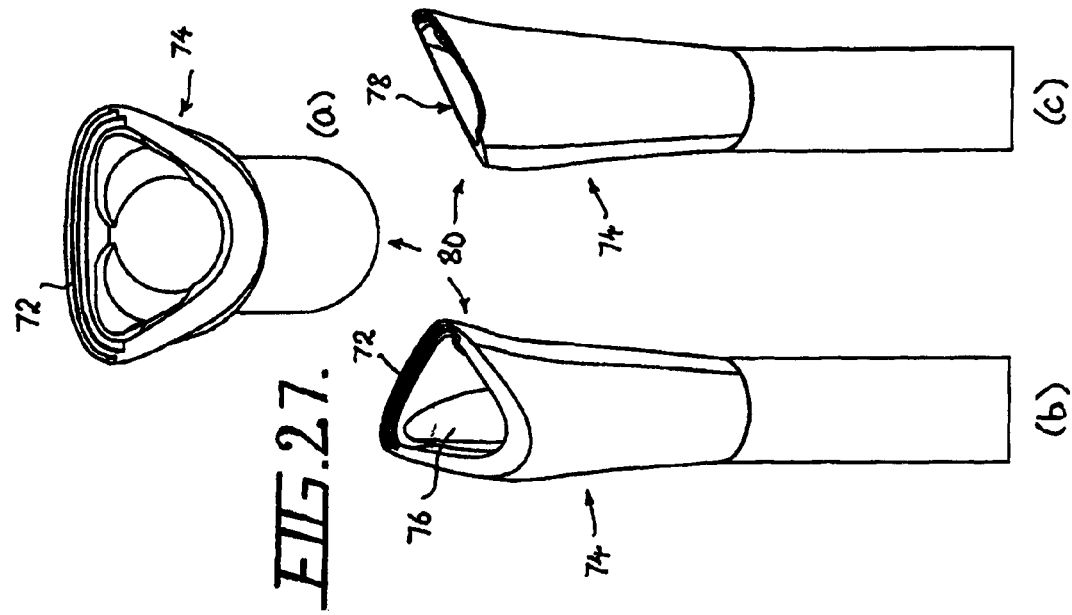
Figure 26:
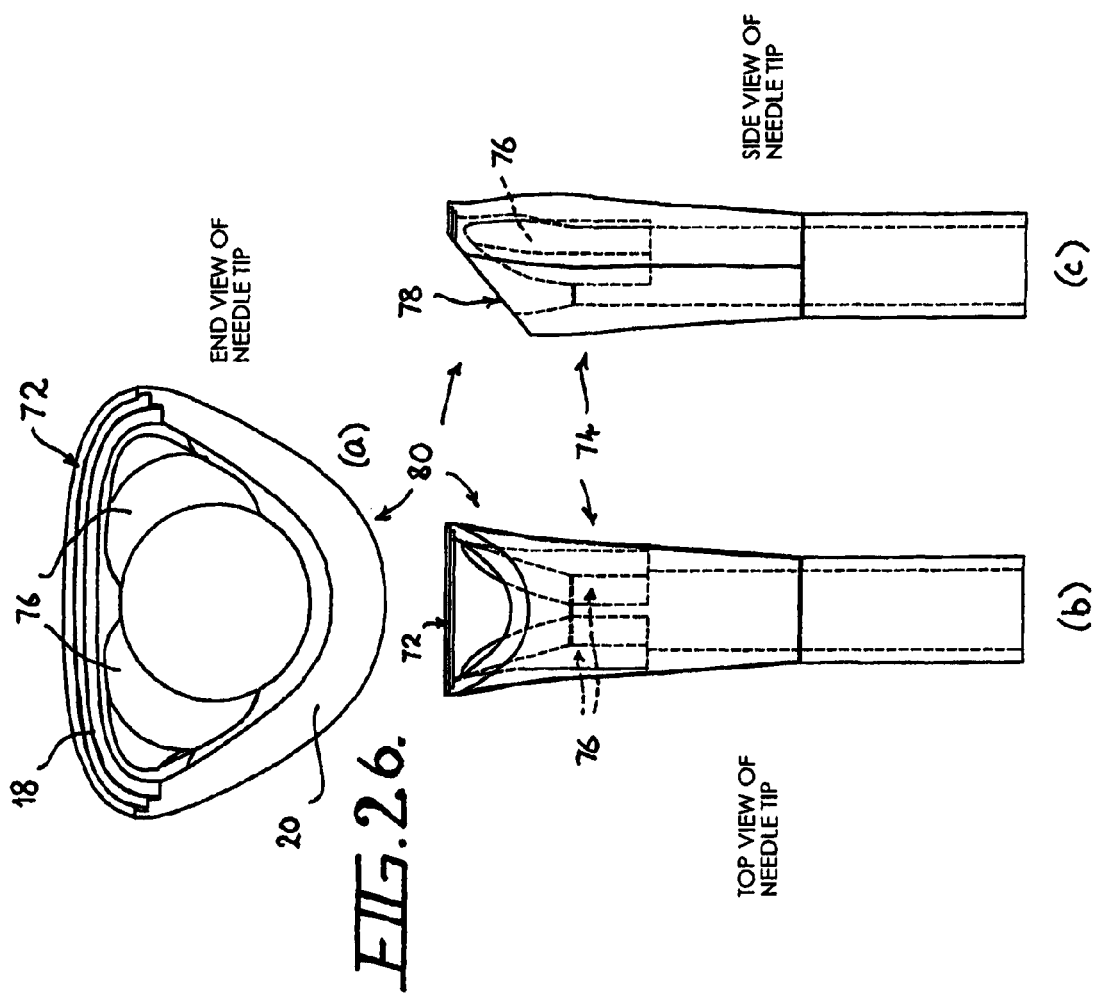
FIGS. 26 (a), (b) and (c) are an enlarged end view, a top view and a side view respectively of an eighth embodiment of a needle tip in accordance with the present invention; and, FIGS. 27 (a), (b) and (c) are an end perspective view, a top perspective view and a side perspective view respectively of the needle tip of FIG. 26.

FIGS. 26 and 27 illustrate an eighth embodiment of a needle 80 for a surgical instrument for removal of diseased or unwanted tissue in accordance with the invention. The needle 80 is similar to the seventh embodiment of FIGS. 24 and 25, and therefore the similar parts will be identified using the same reference numerals, and will not be described again in detail. The main difference in the needle 80 is that a plurality of grooves 76 is milled into a part of the internal surface of the flattened posterior lip 18 of the tip mouth 22.

FIG. 26 (c) illustrates an increased wall thickness in the flared region of needle tip. This provides more material and therefore more flexibility in choice of depth and shape when milling both the longitudinal grooves 76 and transverse grooves 72. The milled longitudinal grooves 76 in the internal surface of the posterior wall of the needle tip reduce the wall thickness in this region. This helps to facilitate flattening of the posterior surface of the needle tip during the manufacturing process.

Lastly all of these offset, asymmetric lip, throat and transverse grooves may be combined with an asymmetric mouth configuration to provide efficient cutting and fluidics. This enhances the effect of transversal or torsional motion at the lip of the tip mouth, and disperses the ultrasonic energy in a different pattern to improve emulsification.

Crenations and lip curl effects may be usefully combined with lip serrations and grooves to further enhance the cutting efficiency. Multiple lip in-curls or in-curves may also be useful, particularly in asymmetric configurations. The effect is to extend the creases so produced down the throat and around the lip dispersing the ultrasonic energy within the mouth in a more turbulent way enhancing the emulsification effect.

Now that several embodiments of the surgical needle tip have been described in detail, it will be apparent that the embodiments provide a number of advantages over the prior art, including the following:

(i) Improved efficiency in cataract removal compared with a conventional tip (as less energy is put into the eye for phacoemulsification because of better cutting action).

(ii) Less disruption during the procedure due to tip blockage.

(iii) Enhanced fluidics at the tip mouth, prevent clogging, as well as inhibiting interruption to flow from standing waves and other harmonics within the tip mouth and throat.

(iv) Good visualisation of the tip mouth and instrument handling ergonomics for the surgeon performing the phacoemulsification procedure.

It will be readily apparent to persons skilled in the relevant arts that various modifications and improvements may be made to the foregoing embodiments, in addition to those already described, without departing from the basic inventive concepts of the present invention. For example, in all of the above described embodiments the grooves milled into the internal surface of the tip are of generally arcuate semicircular cross-sectional shape. However it will be understood that the grooves may be of any suitable cross-sectional shape. Furthermore, in the described embodiments the transverse grooves are milled into an edge of the lip of the needle tip, to form a stepped edge. However it will be appreciated that the transverse grooves may also be milled into the internal surface of the lip mouth set back from the edge of the tip and extending substantially parallel to the edge of the tip mouth. Therefore, it will be appreciated that the scope of the invention is not limited to the specific embodiments described.

The invention claimed is:

1. A needle for a surgical instrument for removal of diseased or unwanted tissue, the needle comprising:
a hollow elongate needle shaft having a needle tip at a distal end for cutting tissue, the needle tip being continuously flared in at least one plane and having a flattened posterior lip and an anterior lip shaped to produce an asymmetric tip mouth with a major axis larger than an outer diameter of the needle shaft and a minor axis smaller than the major axis, the tip mouth being asymmetric about the major axis, a plurality of grooves provided in only part of a surface of the tip in a surface of the posterior lip to form an asymmetric arrangement around the circumference of the needle tip, wherein the tip mouth of the tip has a variable wall thickness.

2. A needle for a surgical instrument as defined in claim 1, wherein the grooves are milled into an internal surface of the tip.

3. A needle for a surgical instrument as defined in claim 1, wherein the grooves are milled into an internal surface adjacent and/or extending to an edge of the posterior lip of the tip mouth.

4. A needle for a surgical instrument as defined in claim 3, wherein the grooves extend substantially perpendicularly to the edge of the posterior lip.

5. A needle for a surgical instrument as defined in claim 3, wherein the grooves extend substantially transversely to a central longitudinal axis of the needle shaft.

6. A needle for a surgical instrument as defined in claim 1, wherein a throat is defined where the needle tip joins the needle shaft, and second grooves are milled into a part of the throat.

7. A needle for a surgical instrument as defined in claim 1, wherein the grooves are straight and substantially parallel to each other.

8. A needle for a surgical instrument as defined in claim 7, wherein the grooves are of all substantially equal width and length.

9. A needle for a surgical instrument as defined in claim 7, wherein the grooves are of unequal width.

10. A needle for a surgical instrument as defined in claim 7, wherein the grooves are spaced from each other at substantially equal intervals.

11. A needle for a surgical instrument as defined in claim 7, wherein the grooves are spaced from each other at unequal intervals.

12. A needle for a surgical instrument as defined in claim 7, wherein the grooves are of a size and shape to create a scalloped effect.

13. A needle for a surgical instrument as defined in claim 1, wherein the anterior lip is curved and the tip mouth is substantially D-shaped.

14. A needle for a surgical instrument as defined in claim 13, wherein the flattened posterior lip is on an edge of a posterior surface that lies in a plane that is substantially parallel to a central longitudinal axis of the needle shaft.

15. A needle for a surgical instrument as defined in claim 14, wherein the needle tip has a central longitudinal axis which is substantially parallel to the central longitudinal axis of the needle shaft.

16. A needle for a surgical instrument as defined in claim 15, wherein the anterior lip of the tip mouth is also flattened and is on the edge of an anterior surface that lies in a plane that is substantially parallel to the central longitudinal axis of the needle shaft.

17. A needle for a surgical instrument as defined in claim 16, wherein the substantially D-shaped tip mouth lies in a plane that is substantially orthogonal to the central longitudinal axis of the needle shaft.

18. A needle for a surgical instrument as defined in claim 16, wherein the posterior lip is substantially transverse to the minor axis of the tip mouth and is on the edge of the posterior surface which is substantially parallel to the major axis of the tip mouth.

19. A needle for a surgical instrument for removal of diseased or unwanted tissue, the needle comprising:
a hollow elongate needle shaft having a central longitudinal axis and a needle tip at a distal end for cutting tissue, the needle tip being continuously flared and having a flattened posterior lip and an anterior lip shaped to produce an asymmetric tip mouth with a major axis larger than an outer diameter of the needle shaft and a minor axis smaller than the major axis, the tip mouth being asymmetric about the major axis, and having a transverse groove milled into only part of a lip of the tip substantially transverse to the central longitudinal axis and in an asymmetric arrangement around the circumference of the needle tip, wherein the tip mouth of the tip has a variable wall thickness.

20. A needle for a surgical instrument as defined in claim 19, wherein the transverse groove is milled into an edge of the lip to form a stepped edge at the tip mouth.

21. A needle for a surgical instrument as defined in claim 20, wherein the transverse groove is one of a plurality of transverse grooves milled into the edge of the lip.

22. A needle for a surgical instrument as defined in claim 19, wherein the needle tip is flared in at least one plane.

23. A needle for a surgical instrument as defined in claim 19, wherein the transverse groove is milled into an edge of the posterior lip.

\* \* \* \* \*